(12) United States Patent
Carlson

(10) Patent No.: US 6,366,811 B1
(45) Date of Patent: *Apr. 2, 2002

(54) EXTRACTION OF HEMODYNAMIC PULSE PRESSURE FROM FLUID AND MYOCARDIAL ACCELERATIONS

(75) Inventor: Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/475,860

(22) Filed: Dec. 30, 1999

Related U.S. Application Data

(63) Continuation of application No. 09/170,375, filed on Oct. 13, 1998, now Pat. No. 6,026,324.

(51) Int. Cl.⁷ ............................................. A61N 1/365
(52) U.S. Cl. ...................... 607/27; 607/17; 607/23; 600/485; 600/526; 600/513
(58) Field of Search .................. 607/9, 27, 18–20, 607/23, 17; 600/519, 513, 483, 485, 509, 526

(56) References Cited

U.S. PATENT DOCUMENTS

| 4,566,456 | A | | 1/1986 | Koning et al. ........ 128/419 PG |
| 5,156,147 | A | | 10/1992 | Warren et al. ........ 128/419 PG |
| 5,480,412 | A | * | 1/1996 | Mouchawar et al. ........... 607/6 |
| 5,549,650 | A | | 8/1996 | Bornzin et al. ................ 607/24 |
| 5,628,777 | A | * | 5/1997 | Moberg et al. .............. 607/122 |
| 5,674,256 | A | | 10/1997 | Carlson ........................ 607/17 |

* cited by examiner

Primary Examiner—Kennedy Schaetzle
(74) Attorney, Agent, or Firm—Nikolai & Mersereau, P.A.

(57) ABSTRACT

A cardiac stimulating apparatus and method is described that non-intrusively determines an amount indicative of hemodynamic pulse pressure from an accelerometer signal. The amount indicative of pulse pressure is determined over several cardiac cycles and is used to optimize cardiac performance by evaluating the amount indicative of pulse pressure over varying timing intervals. The timing intervals are measured between at least one of intrinsic and paced stimulations of pre-selected chambers of the heart and a maximum pulse pressure indicates the optimum timing interval under manipulation. The cardiac stimulating apparatus and method may be used in any of several pacing modes including A-V pacing, V-V pacing, or A-A pacing.

28 Claims, 5 Drawing Sheets

EXTRACTION OF HEMODYNAMIC PULSE PRESSURE FROM FLUID AND MYOCARDIAL ACCELERATIONS

This is a continuation application of application Ser. No. 09/170,375, filed on Oct. 13, 1998 now U.S. Pat. No. 6,026,324.

BACKGROUND OF THE INVENTION

I. Field of the Invention

This invention relates generally to an implantable, programmable, cardiac stimulating apparatus and method that non-intrusively determines the pulse pressure of a patient's heart. The determined pulse pressure may be utilized, for example, to enhance cardiac performance. The cardiac performance may be enhanced by first manipulating the pacing rate and pacer timing intervals between intrinsic or paced stimulations of pre-selected chambers of the patient's heart over a plurality of periods, then determining the pulse pressure during each period, identifying the pacer timing interval and/or pacing rate that results in the greatest pulse pressure, and finally setting the cardiac stimulator to the timing interval associated with the greatest pulse pressure to thereby increase cardiac performance.

II. Discussion of the Related Art

The cardiac output of a patient's heart may be reduced as a result of defects, failure, disease, ageing, or other cardiac disorders or anomalies. Reduced cardiac output can lead to shortness of breath, restricted movement, and even death. Over the years various devices including pacers and defibrillators have been used to assist and/or alter the intrinsic contractions and pacing of the heart in order to increase the cardiac output of the heart. The pacer, for example, typically includes a pulse generator, power supply, microprocessor based controller, and an electrical lead of suitable construction coupled to the pulse generator for unipolar or bipolar pacing.

Various methods have been devised to maximize cardiac output, wherein the maximum cardiac output is correlated with a measured pulse pressure. Typically, the pulse pressure is measured via cardiac catheterization or through a pressure sensor positioned on a lead. A pacer of suitable construction is required in order to receive a signal from the pressure sensor and correlate the received signal with cardiac output. At times it may become necessary to replace an already implanted pacemaker with a pacer capable of correlating the maximum cardiac output with the measured pulse pressure. Ideally, replacement of the pacer would not require placement of additional leads or lead ablation and replacement.

In U.S. Pat. 4,566,456 issued to Koning et al., a device is described that adjusts a pacer rate relative to right ventricular systolic pressure. The right ventricular systolic pressure is measured by a piezoelectric pressure sensor mounted on a lead. Koning et al. does not provide for a device or method that non-intrusively determines the pulse pressure of a patient's heart. The Koning et al. device requires a lead having a pressure sensor coupled thereto, and thus requires replacement or use of the specialized lead in conjunction with the disclosed pacer.

In U.S. Pat. 5,549,650 issued to Bornzin et al., a device is described for providing hemodynamically optimal pacing therapy. The device apparently includes a cardiac wall motion sensor which must be incorporated into an implantable lead. The rate of pacing therapy is controlled by the Bornzin et al. device as a function of the cardiac wall velocity signals and cardiac wall displacement signals (mechanical activities of the heart generally) transmitted by the cardiac wall motion sensor. The Bornzin et al. device does not provide hemodynamically optimal pacing therapy by non-invasively measuring the hemodynamic pulse pressure of the heart. The Bornzin et al. device requires replacement or use of a specialized lead in conjunction with its pacing device. Hence, there is a need for a pacemaker that non-intrusively determines the pulse pressure of a patient's heart. The present invention addresses these and other needs.

SUMMARY OF THE INVENTION

In accordance with the present invention, a cardiac stimulation device is provided which is capable of non-intrusively determining a hemodynamic pulse pressure of the patient's heart. The cardiac stimulating device may be programmed to function in a preset pacing mode having a preset pacing rate and timing interval to optimize cardiac performance of a patient's heart. The cardiac stimulation device is capable of operating in any of a plurality of pacing modes, including A-V pacing, V-V pacing and A-A pacing, wherein the A-V pacing mode may include $A_R$-$V_R$ pacing, $A_R$-$V_L$ pacing, $A_L$-$V_R$ pacing, $A_R$-$V_{RL}$ pacing, $A_L$-$V_{RL}$ pacing, and $A_L$-$V_L$ pacing.

The cardiac stimulation device includes a pulse generator for stimulating a patient's heart in a preselected pacing mode, a power supply, a microprocessor-based controller, and an accelerometer sensor, all of which are enclosed in an implantable casing. An internal or external cardiac electrogram or other conventional device for identifying cardiac cycles of a patient's heart is coupled to the microprocessor based controller. The microprocessor-based controller is coupled to both the accelerometer and the pulse generator for receiving an input from the former and providing control signals to the latter.

The accelerometer sensor is electrically coupled to the microprocessor based controller and the accelerometer transmits a signal to the controller associated with fluid and myocardial accelerations of the patient's heart. A filtering means is coupled to the accelerometer for filtering and conditioning the signal transmitted by the accelerometer to produce a waveform related to a pulse pressure within the patient's heart.

The microprocessor based controller includes a linear prediction means (utilizing Levinson's Algorithm well known to those skilled in the art) which predicts values associated with the waveform, wherein the linear prediction means includes a means for auto-regressive analysis of the preconditioned accelerometer energy signal using an algorithm which is described below in greater detail. The microprocessor based controller also includes: a bandwidth determining means for determining a bandwidth from predicted values of the waveform, center frequency determining means for determining a center frequency from predicted values of the waveform, means for calculating an amount indicative of pulse pressure from the determined bandwidth and center frequency, and analyzing means for analyzing the amounts indicative of pulse pressure over corresponding cardiac cycles.

The calculated value associated with pulse pressure may be analyzed by the microprocessor over a preselected number of cardiac cycles and for a plurality of preselected timing intervals, wherein the timing interval is a measured time between at least one of intrinsic and paced stimulations of pre-selected chambers of the heart. The value associated with pulse pressure corresponding with each timing interval is then compared to determine which timing interval results in the greatest pulse pressure. The pacer may then automatically reset the timing interval to this "maximum" timing interval.

The analysis and comparison of the accelerometer signal preferably occurs when the patient is at rest, the quiescent period. The accelerometer signal may also be used to determine the period of quiescent activity. Analyzing the accelerometer signal during the period of quiescent activity minimizes motion artifact in the accelerometer signal. Further, analyzing the signal during the period of quiescent activity allows the measurements to be taken during relative steady state hemodynamic conditions.

Those skilled in the art will recognize that the accelerometer and other components may be mounted externally, linking these components with the microprocessor by telemetry. However, without limitation, a single self-contained implantable cardiac stimulating device including all of these components is preferred.

OBJECTS

It is accordingly a principal object of the present invention to provide a cardiac stimulation device capable of dual chamber pacing which non-intrusively determines a value indicative of the pulse pressure for a selected cardiac cycle.

Another object of the present invention is to provide a cardiac stimulator which maximizes cardiac performance through non-invasive means by determining a value indicative of the cardiac pulse pressure from a signal of an accelerometer.

A further object of the present invention is to optimize cardiac performance based on an analysis and comparison of non-intrusively measured values indicative of pulse pressure over a plurality of preselected timing intervals, to thereby determine the optimum timing interval of the cardiac stimulator.

Still another object of the present invention is to provide a method for optimizing cardiac performance by non-intrusively determining the optimal timing interval based on the mechanical performance of the patient's heart.

These and other objects as well as these and other features and advantages of the present invention will become readily apparent to those skilled in the art from a review of the following detailed description of the preferred embodiment especially when considered in conjunction with the claims and accompanying drawings in which like numerals in the several views refer to corresponding parts.

DETAILED DESCRIPTION OF THE PREFERRED EMBODIMENT

Figure 1:
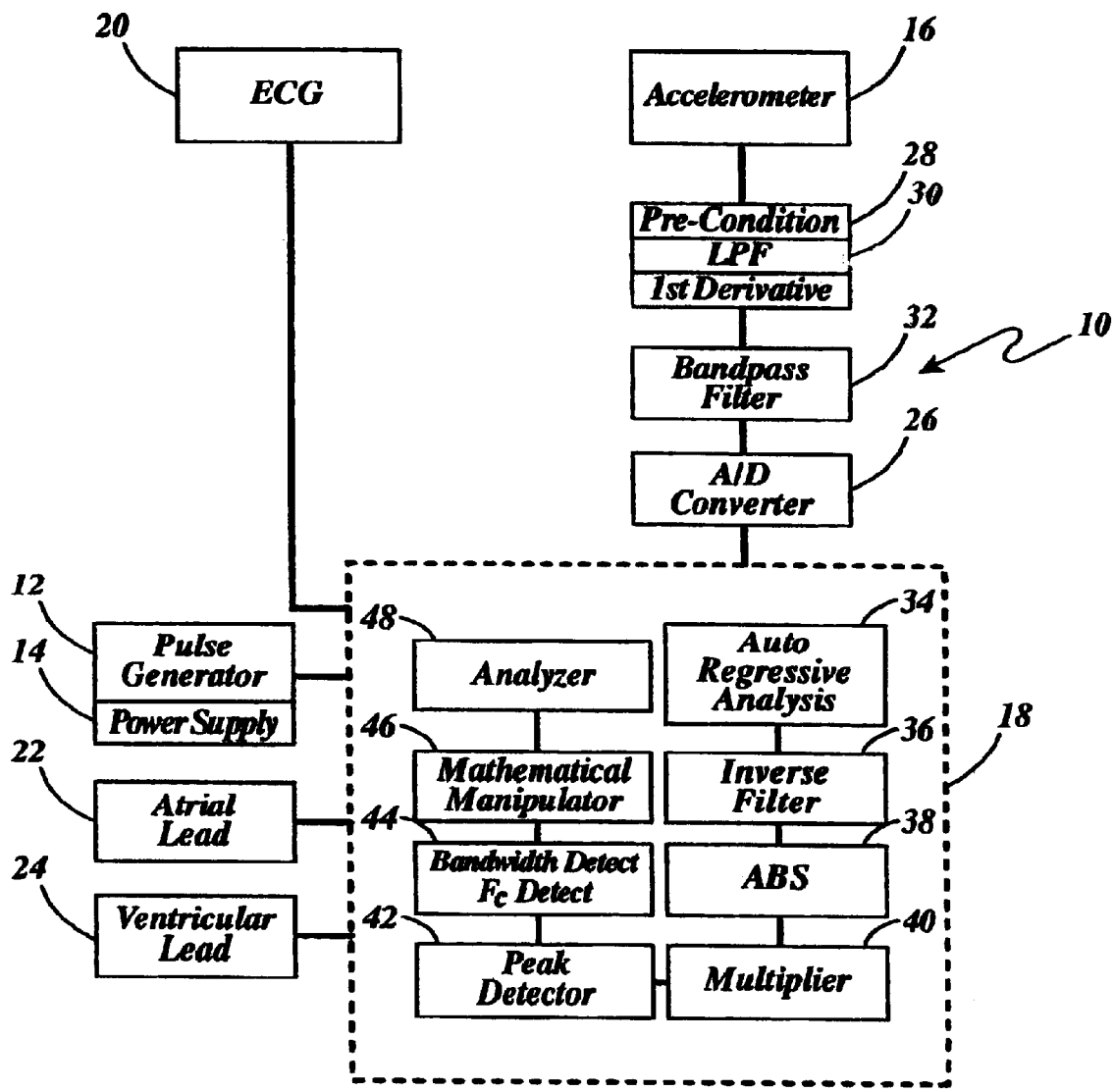
FIG. 1 is a block diagram of a portion of the electrical components of a cardiac stimulator of the present invention coupled to an atrial lead and a ventricular lead.

Referring first to FIG. 1, there is generally shown in block diagram the cardiac stimulator 10 of the present invention. The cardiac stimulator 10 includes a pulse generator 12 having a power supply 14, an accelerometer 16, a microprocessor based controller (represented by a dotted line) 18, and an electrocardiogram (ECG) 20. The ECG 20 may be a surface or internal electrogram of known suitable construction. A portion of the electrical components of the microprocessor based controller 18 are shown enclosed by the dotted line representing the microprocessor based controller 18. Atrial and ventricular leads 22 and 24 are shown coupled to the microprocessor based controller 18.

The microprocessor 18 controls the cardiac stimulating pulses delivered by pulse generator 12 to one or both of the leads 22 and 24, depending upon the pacing mode selected. Further, the microprocessor based controller 18 establishes the optimal timing interval between at least one of intrinsic or paced stimulations of pre-selected chambers of the heart. The timing interval to be optimized may include the timing interval between any of the following pacing modes: A-A pacing, the V-V pacing and A-V pacing. A timing interval for A-A pacing refers to the timing between the right and left atrial contractions (either intrinsic or paced), a timing interval for V-V pacing refers to the timing between the right and left ventricular contractions (either intrinsic or paced), and a timing interval for A-V pacing refers to the timing between atrial and ventricular contractions (either intrinsic or paced), when sensing/pacing in any one of the following configurations: $A_R$-$V_R$ pacing, $A_R$-$V_L$ pacing, $A_L$-$V_R$ pacing, $A_R$-$V_{RL}$ pacing, $A_L$-$V_{RL}$ pacing, and $A_L$-$V_L$ pacing.

Cardiac stimulating devices capable of telemetering various status information including selecting a pacing mode and other parameters including the timing interval (determined by the physician), are commercially available from, for example Cardiac Pacemakers, Inc., St. Paul, Minn. An external programmer having a microprocessor and associated memory may transmit information in a conventional way through a telemetry link and transmission receiver 48 of the cardiac stimulator's microprocessor. Using the programmer and the telemetry link, operating parameter values for the cardiac pacer can be delivered to it by a cardiologist for setting the cardiac cycle pacing parameter values to be utilized, including the timing interval.

The microprocessor 18 further has both RAM (random access memory), and ROM (read only memory) for storing programs and data, which allows generally: the processing of a signal from an electrogram, processing of signals transmitted from the accelerometer 16, storing various information derived from the processing, and changing the preset constants of the program.

The accelerometer 16 is positioned within the casing of the cardiac stimulator or pacer and is coupled to the microprocessor based controller 18 through an analog/digital convertor 26 and filters further described below. The accelerometer 16 provides a signal that is processed to provide a non-intrusive measure of pulse pressure during a cardiac cycle. The casing of the cardiac pacer 10 is implanted in a surgically made pocket, typically in either the left or right shoulder region of the patient. By positioning the accelerometer 16 in the casing (not shown) of the cardiac pacer 10, the accelerometer 16 generates a global signal associated with various atrial and ventricular events. A globalized signal is preferred over a localized signal (a signal transmitted from an accelerometer in direct contact with an outer wall of the heart). The signal from the accelerometer 50 may also be used to evaluate levels of physical activity, thereby identifying periods in which physical activity is low.

An analog signal of the accelerometer 16 comprises events associated with heart sounds, compressions, blood fluid motions and/or cardiac wall accelerations and decelerations caused from cardiac activity along with motion artifacts and respiratory events. Intermediate the accelerometer 16 and the microprocessor based controller 18 a preconditioning filter 28, low pass filter 30, bandpass filter 32 and analog-to-digital (A/D) converter 26 are electrically coupled therebetween. The raw or analog signal transmitted from the accelerometer 16 passes through the preconditioning filter 28 and low pass filter 30 to produce a first derivative of the low pass filter signal.

The first derivative of the low pass filter signal then passes through a bandpass filter and is digitized by an analog to digital (A-D) converter at 26. Preconditioning and filtering of the accelerometer signal enhances the pre-ejection accelerometer signature portion of the signal that is due to the on-set of ejection and further filters out other extraneous events. In this manner, a waveform is produced representative of pulse pressure, eliminating non-essential frequencies utilizing the bandpass filter 32 and eliminating the higher frequency components utilizing the low pass filter 30. The digital waveform is then transmitted from the A/D converter 26 to the microprocessor based controller 18, wherein the waveform first passes through an auto regressive analysis 34 using well-known Levinson or the Yule-Walker algorithms from autocorrelation lags of the accelerometer signal derived during the time of the main lobe of the energy signal. A discrete set of reflection coefficients representing the reference signal result. This coefficient set is fed to an inverse linear filter predictor 36.

The resulting coefficients then pass through an inverse linear predictor filter which produces an output indicative of the intensity or ongoing intensity energy level of the accelerometer signal as a function of time. The absolute value of this output is then subjected to a multiplier 40. The time of maximum absolute value of the spike corresponds to the time of minimum error with respect to the beginning of ejection. The preferred implementation of the inverse filter is that of an FIR lattice filter. This implementation results in a structure that is maximally numerically stable, since stable filters result in coefficient multiplication operations that are bounded in absolute value by 1.

The peak detector 42 is enabled and then a bandwidth and the center of frequency detectors identify values associated with the bandwidth and center of frequency ($F_c$). Once a value for the bandwidth and $F_c$ have been determined, then a mathematical manipulator 46 determines a value indicative of pulse pressure from these values. The value indicative of pulse pressure is repeatedly determined over a predetermined number of respiratory cycles and then a mean, maximum, or average value indicative of pressure may be determined. An analyzer 48 compares for example, the maximum value indicative of the pulse pressure for several preset pacing intervals and thereby determines the pacing interval which results in the greatest pulse pressure immediately before ejection. The microprocessor based controller 18 then sets the timing interval to the determined interval. Those skilled in the art will appreciate that the adjustment in timing interval may be programmed to occur periodically or at a specific time each day.

Figure 2:
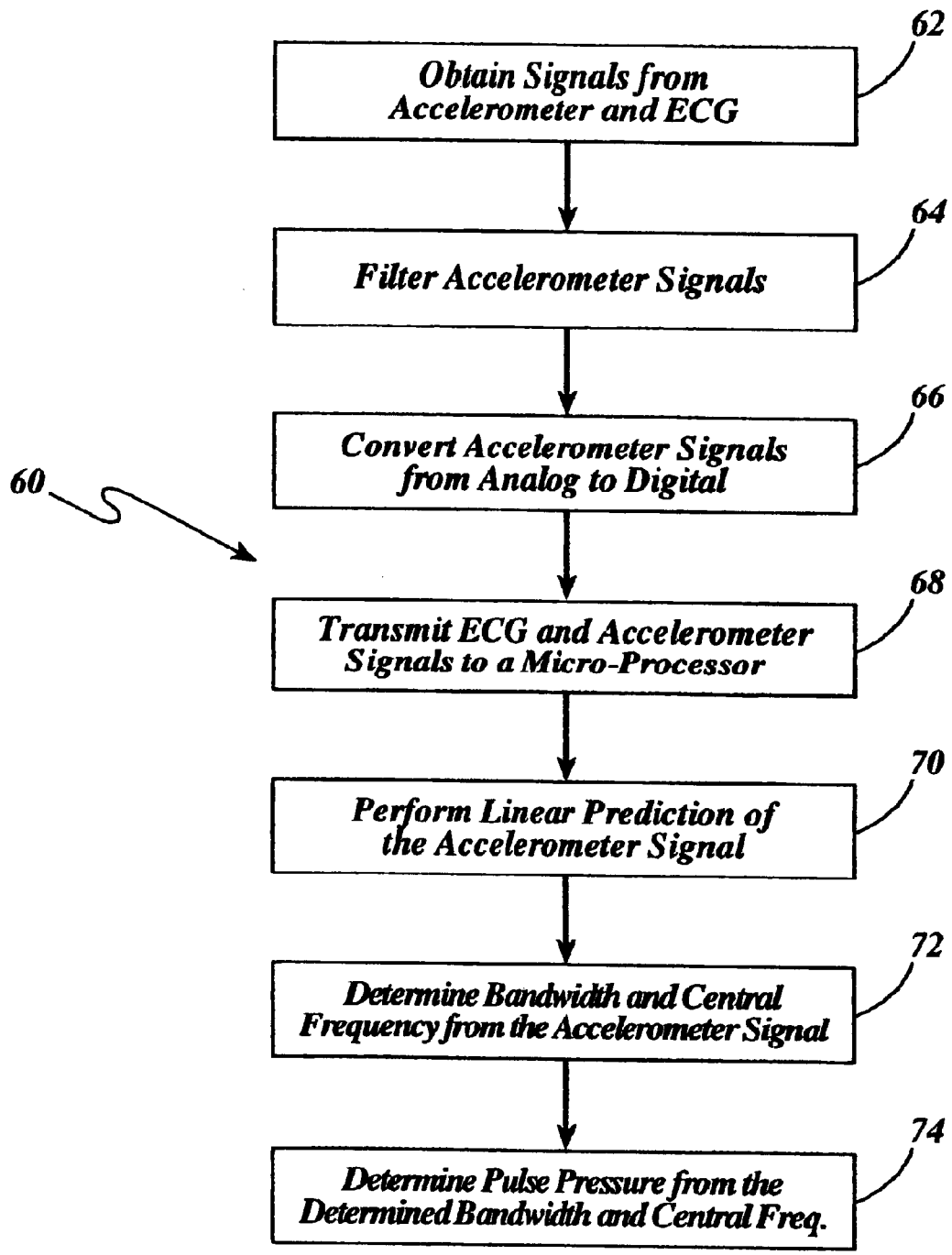
FIG. 2 is a flow diagram of the steps used by the microprocessor based controller to determine the pulse pressure from a signal transmitted by an accelerometer positioned within the casing of a cardiac stimulator.

In further explaining the invention, and especially the flow chart of FIG. 2, it is assumed that the timing interval of the cardiac stimulation device 10 is preset to correlate the pulse pressure with the atrial-ventricular (A-V) interval. It should be emphasized that the invention is not to be limited to use in a system where only the A-V delay interval is adjusted, and the results of the adjustment on pulse pressure noted. Those skilled in the art will recognize that the algorithm described equally applies to other timing intervals for any of a number of pacing modes. For example, the lower rate limit interval (R-R), the interval between right and left atrial stimulations ($A_R$-$A_L$ interval), the interval between right and left ventricular stimulations ($V_R$-$V_L$ interval), $A_R$-$V_R$ interval, $A_L$-$V_R$ interval, $A_R$-$V_{RL}$ interval, $A_L$-$V_{RL}$ interval, $A_L$-$V_L$ interval etc. may be subjected to periodic changes with the effects on the pulse pressure being noted and stored.

The algorithm 60 used to non-intrusively extract the hemodynamic pulse pressure from an accelerometer signal is shown in FIG. 2. Initially, signals from both the accelerometer 16 and ECG 20 are initiated to produce signals corresponding to the cardiac motion and cardiac cycles (see Block 62). The signal produced by the ECG is used to correlate a measured pulse pressure with the cardiac cycle. The accelerometer's 16 signal is then transmitted through a series of filters as described above, to remove ancillary information contained in the accelerometer signal (see block 64). The filtered analog accelerometer signal is then converted to a digital signal (see block 66). The digital signal and ECG signal are transmitted to the microprocessor based controller 18 (see block 68) for processing and analysis. The microprocessor based controller 18 then performs a linear prediction from the digital signals resulting in $K_1$ and $K_2$ and thereafter determines the $F_B$ (bandwidth) and $F_C$ (central frequency) of the linear prediction (see blocks 70 and 72), where $F_C$ is determined from the following:

$$\theta_F = \frac{-K(1 + K_2)}{\sqrt{K_2}} \text{ and,}$$

$$F_C = \frac{[\cos^{-1}(\theta_F)]}{2\pi}$$

and $F_B$ is determined from the following equations:

$$p = \sqrt{K_2} \text{ and}$$

$$\theta_B = \frac{[4p - (1 - p^2)]}{2p} \text{ and}$$

$$F_B = \frac{[\cos^{-1}(\theta_B)]}{\pi}$$

The determined bandwidth and center frequency are added to obtain a value associated with the pulse pressure (see block 74). As previously recognized, the non-intrusively determined pulse pressure may be utilized to enhance cardiac performance. By means of example, immediately below is a description of one method of utilizing the calculated pulse pressure to enhance cardiac performance.

An ordered set of pre-set A-V interval values may be programmed into the memory of the microprocessor based controller 18 at the time of implant by the physician. This timing interval set would contain a range of A-V interval values over which the unit will automatically switch. Oftentimes, the sequence of the set may comprise alternation between a baseline without pacing (intrinsic) and a randomly selected A-V interval (having a value somewhat less than the intrinsic A-V interval). This alternation reduces hysteresis and other effects that a previous A-V interval value may have on the next A-V interval.

The microprocessor receives a digitized accelerometer signal from the accelerometer. A portion of this signal represents the level of physical activity of the patient. An initial test may be made to determine whether the physical activity is less than a predetermined amount X, which is indicative of a patient at rest. When the patient is resting, the accelerometer readings are less subject to noise and motion artifacts.

When the physical activity is less than the predetermined amount X, the A-V interval index m is then set to 1. The A-V interval is periodically changed, determining the value indicative of pulse pressure over several cardiac cycles for each A-V interval. The microprocessor 18 simultaneously analyzes the electrogram 20 signal to thereby correlate the determined value indicative of pulse pressure with the respiratory cycles determined from the ECG signal. The microprocessor based controller 18 then compares values indicative of pulse pressure for each iterated A-V interval to determine which A-V interval setting results in the greatest value indicative of pulse pressure. The A-V interval setting is then set by the microprocessor based controller 18 to the optimum A-V interval value. The A-V interval remains at this optimum setting until a predetermined time period Z has passed. The analysis is then repeated to determine a new optimum A-V interval.

Figure 3:
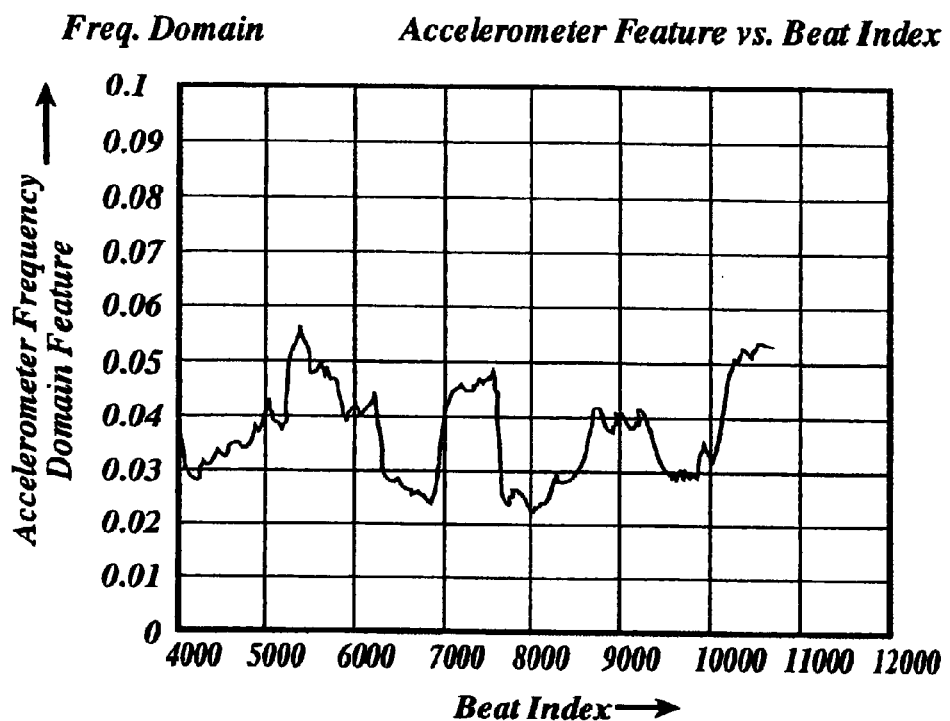
FIG. 3 is a graph of a frequency domain feature plotted over time (beat index) and extracted from an accelerometer signal of a non-intrusive accelerometer.
Figure 4:
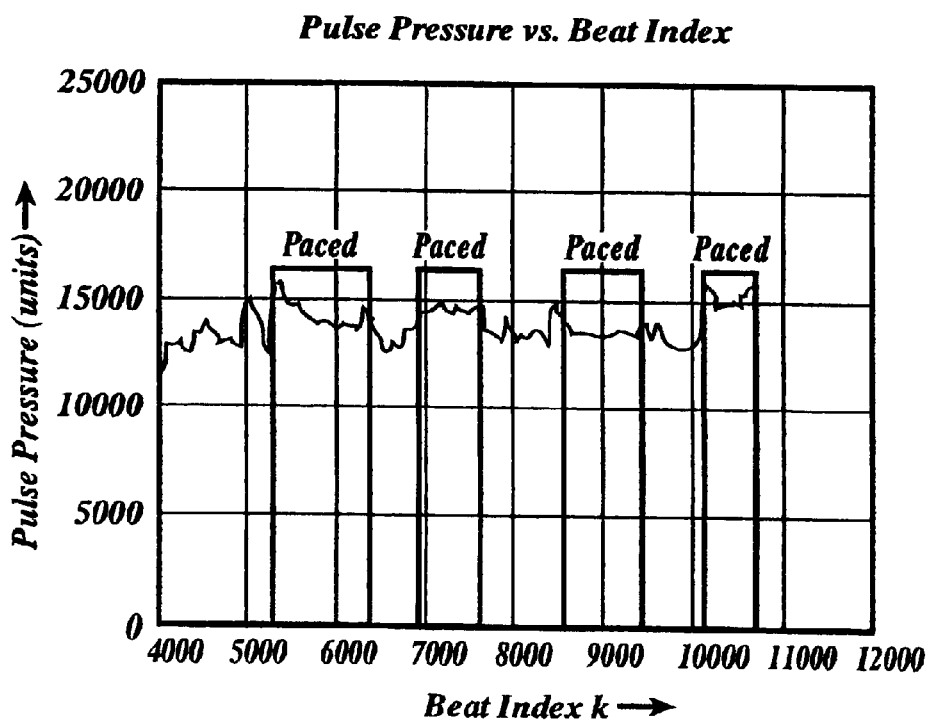
FIG. 4 is a graph of a pulse pressure measured by an independent pulse pressure sensor plotted over the same beat index as FIG. 3 for comparison.
Figure 5:
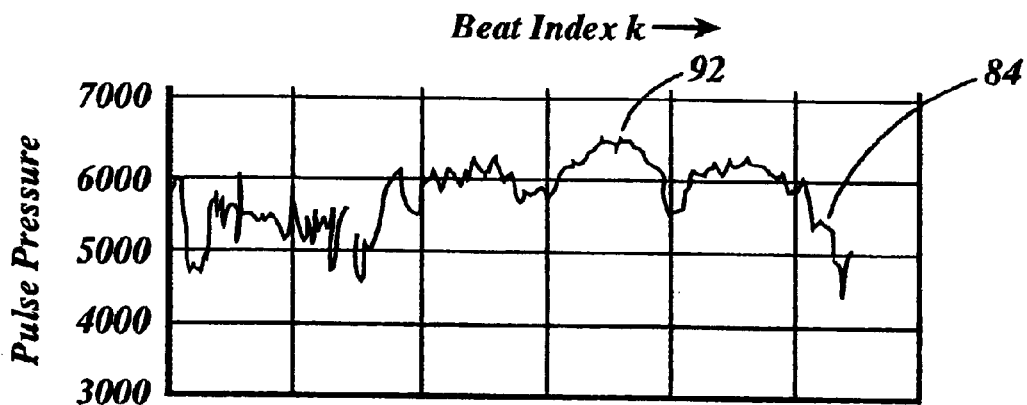
FIG. 5 is a graph of a pulse pressure measured by an independent pulse pressure sensor over a beat index.
Figure 6:
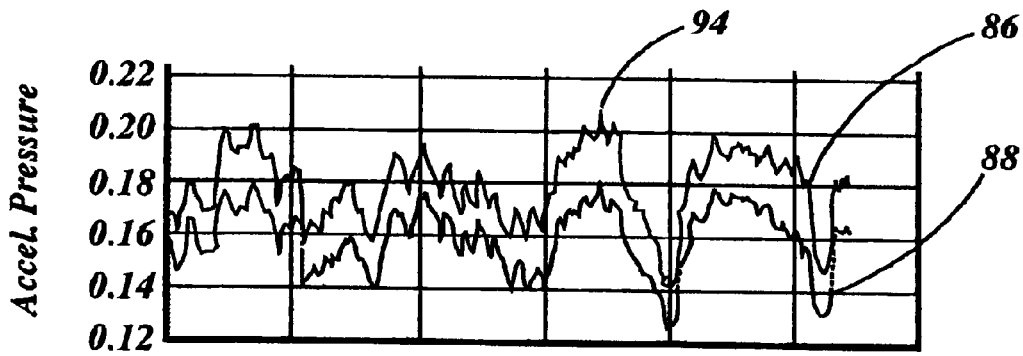
FIG. 6 is a graph of frequency domain features $K_1$ and $K_2$ extracted from an accelerometer signal over the same beat index as FIG. 5, and is shown for comparison.
Figure 7:
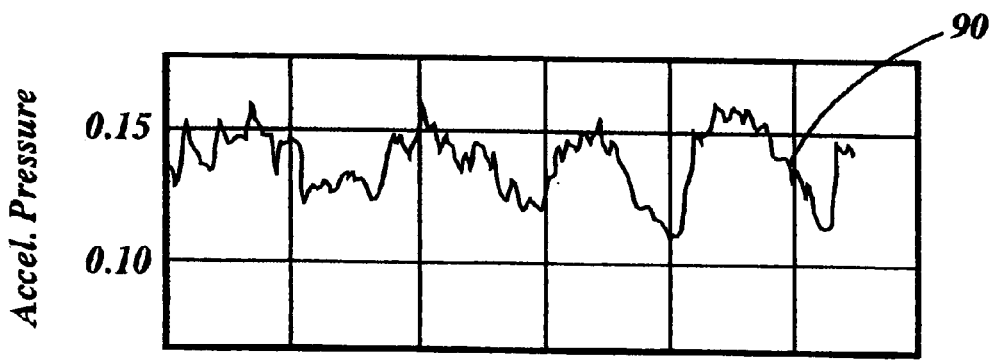
FIG. 7 is another graph of a frequency domain feature extracted from an accelerometer signal and plotted over a beat index.

FIGS. 3–8 are various graphs illustrating graphically that a feature filtered from an accelerometer signal correlates with an independently measured pulse pressure. By filtering the accelerometer signal, a waveform 80 of a specific event feature associated with pulse pressure is separated out from the accelerometer signal and is shown in FIG. 3 plotted over several cardiac cycles. The peaks in FIGS. 3–7 correspond with the ejection of blood fluid. FIG. 4 is a plot 82 of the pulse pressure values measured by a pulse pressure sensor. From a comparison of FIGS. 3 and 4 those skilled in the art will appreciate that the frequency domain feature derived from the accelerometer signal 80 correlates with the measured pulse pressure 82. Likewise, a comparison of FIGS. 5 to FIGS. 6 and 7 illustrates that the peaks of a filtered accelerometer feature 84, 86, and 88 correspond with the peaks of a measured pulse pressure signal 90. Also, it can be seen that the maximum observed pulse pressure 92 in FIG. 5 corresponds with the maximum accelerometer feature 94 in FIG. 6.

Figure 8:
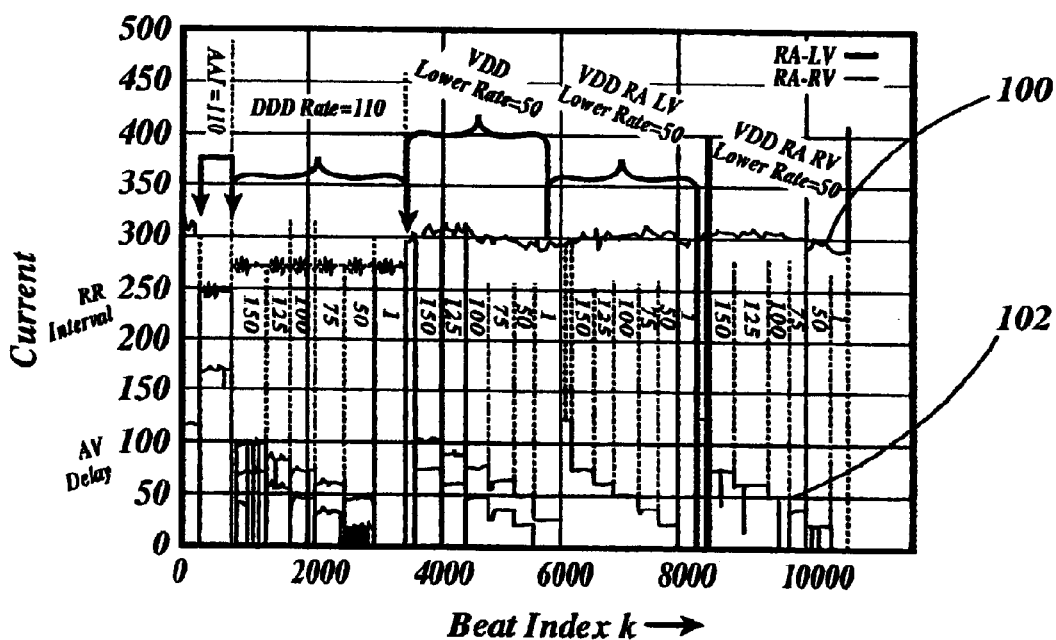
FIG. 8 is a graph of a frequency domain feature plotted over a measured beat index extracted from an accelerometer signal, wherein the programmed pacing mode and delay rate is shown varying over the measured beat index.

FIG. 8 substantiates that for different pacing modes the maximum pulse pressure 100 may be used to identify an optimal timing interval 102. The timing interval 102 observed in FIG. 8 was the A-V interval, however those skilled in the art will appreciate that other timing intervals may also be maximized through correlation with the maximum pulse pressure 100.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A cardiac stimulating apparatus functioning in a preset pacing mode having preset pacing rates and timing intervals, and programmed to optimize cardiac performance of a patient's heart, said cardiac stimulating apparatus comprising:
   a) a pulse generator;
   b) an accelerometer electrically coupled to a controller of the cardiac stimulating apparatus, said accelerometer transmitting a signal associated with fluid and myocardial accelerations of the patient's heart;
   c) filtering means coupled to the accelerometer for filtering and conditioning the signal transmitted by the accelerometer to produce a waveform related to a pulse pressure within the patient's heart; and
   d) said controller including a timing means for identifying cardiac cycles of the patient's heart, a linear prediction means for predicting values associated with the waveform, and means for determining an amount indicative of pulse pressure from said waveform.

2. The cardiac stimulating apparatus as recited in claim 1, whereby the determined amount indicative of pulse pressure is analyzed and compared by said controller over a preselected number of cardiac cycles for a plurality of preselected timing intervals, said timing intervals being a time between at least one of intrinsic and paced stimulations of preselected chambers of the heart, to thereby determine an optimum timing interval.

3. The cardiac stimulating apparatus as recited in claim 1, wherein the linear prediction means further includes a means for auto-regressive analysis of the preconditioned accelerometer energy signal using algorithms selected from the group consisting of Levinson and Yule-Walker.

4. The cardiac stimulating apparatus as recited in claim 1, wherein said controller includes a means for identifying, from the signal transmitted by the accelerometer, a time of physical inactivity.

5. The cardiac stimulating apparatus as recited in claim 1, wherein the dual chamber cardiac pacer functions in a pacing mode selected from the group consisting of A-V pacing, V-V pacing and A-A pacing.

6. The cardiac stimulating apparatus as recited in claim 5, wherein the A-V pacing mode is selected from the group consisting of $A_R$-$V_R$ pacing, $A_R$-$V_L$ pacing, $A_L$-$V_R$ pacing, $A_R$-$V_{RL}$ pacing, $A_L$-$V_{RL}$ pacing, and $A_L$-$V_L$ pacing.

7. The cardiac stimulating apparatus as recited in claim 1, wherein said controller includes bandwidth determining means for determining a bandwidth from predicted values of the waveform.

8. The cardiac stimulating apparatus as recited in claim 7, wherein said controller further includes a center frequency determining means for determining a center frequency from predicted values of the waveform.

9. The cardiac stimulating apparatus as recited in claim 8, wherein said controller determines the amount indicative of pulse pressure from the determined bandwidth and center frequency.

10. The cardiac stimulating apparatus as recited in claim 1, wherein said controller further includes analyzing means for analyzing the amounts indicative of pulse pressure over corresponding cardiac cycles.

11. A cardiac stimulating apparatus functioning in a preset pacing mode having preset pacing rates and timing intervals, and programmed to optimize cardiac performance of a patient's heart, said cardiac stimulating apparatus comprising:

a) a pulse generator;
b) an accelerometer electrically coupled to a controller of the cardiac stimulating apparatus, said accelerometer transmitting a signal associated with fluid and myocardial accelerations of the patient's heart;
c) filtering means coupled to the accelerometer for filtering and conditioning the signal transmitted by the accelerometer to produce a waveform related to a pulse pressure within the patient's heart; and
d) said controller including a timing means for identifying cardiac cycles of the patient's heart and means for determining an amount indicative of pulse pressure from said waveform, said amount indicative of pulse pressure being analyzed and compared by said controller over a preselected number of cardiac cycles for a plurality of preselected timing intervals, said timing intervals being a time between at least one of intrinsic and paced stimulations of pre-selected chambers of the heart, to thereby determine an optimum timing interval.

12. A cardiac stimulating apparatus functioning in a preset pacing mode having preset pacing rates and timing intervals, and programmed to optimize cardiac performance of a patient's heart, said cardiac stimulating apparatus comprising:
a) a pulse generator;
b) an accelerometer electrically coupled to a controller of the cardiac stimulating apparatus, said accelerometer transmitting a signal associated with fluid and myocardial accelerations of the patient's heart;
c) filtering means coupled to the accelerometer for filtering and conditioning the signal transmitted by the accelerometer to produce a waveform related to a pulse pressure within the patient's heart; and
d) said controller including a timing means for identifying cardiac cycles of the patient's heart and means for determining an amount indicative of pulse pressure from said waveform, said means for determining including means for auto-regressive analysis of said waveform using algorithms selected from the group consisting of Levinson and Yule Walker.

13. A cardiac stimulating apparatus functioning in a preset pacing mode having preset pacing rates and timing intervals, and programmed to optimize cardiac performance of a patient's heart, said cardiac stimulating apparatus comprising:
a) a pulse generator;
b) an accelerometer electrically coupled to a controller of the cardiac stimulating apparatus, said accelerometer transmitting a signal associated with fluid and myocardial accelerations of the patient's heart;
c) filtering means coupled to the accelerometer for filtering and conditioning the signal transmitted by the accelerometer to produce a waveform related to a pulse pressure within the patient's heart; and
d) said controller including a timing means for identifying cardiac cycles of the patient's heart, means responsive to the signal transmitted by the accelerometer for identifying a time of physical inactivity and means for determining an amount indicative of pulse pressure from said waveform.

14. A cardiac stimulating apparatus functioning in a preset mode selected from the group consisting of A-V pacing, V-V pacing and A-A pacing and having preset pacing rates and timing intervals, and programmed to optimize cardiac performance of a patient's heart, said cardiac stimulating apparatus comprising:

a) a pulse generator;
b) an accelerometer electrically coupled to a controller of the cardiac stimulating apparatus, said accelerometer transmitting a signal associated with fluid and myocardial accelerations of the patient's heart;
c) filtering means coupled to the accelerometer for filtering and conditioning the signal transmitted by the accelerometer to produce a waveform related to a pulse pressure within the patient's heart; and
d) said controller including a timing means for identifying cardiac cycles of the patient's heart and means for determining an amount indicative of pulse pressure from said waveform.

15. The cardiac stimulating apparatus as recited in claim 14, wherein the A-V pacing mode is selected from the group consisting of $A_R$-$V_R$ pacing, $A_R$-$V_L$ pacing, $A_L$-$V_R$ pacing, $A_R$-$V_{RL}$ pacing, $A_L$-$V_{RL}$ pacing, and $A_L$-$V_L$ pacing.

16. A cardiac stimulating apparatus functioning in a preset pacing mode having preset pacing rates and timing intervals, and programmed to optimize cardiac performance of a patient's heart, said cardiac stimulating apparatus comprising:
a) a pulse generator;
b) an accelerometer electrically coupled to a controller of the cardiac stimulating apparatus, said accelerometer transmitting a signal associated with fluid and myocardial accelerations of the patient's heart;
c) filtering means coupled to the accelerometer for filtering and conditioning the signal transmitted by the accelerometer to produce a waveform related to a pulse pressure within the patient's heart; and
d) said controller including a timing means for identifying cardiac cycles of the patient's heart, bandwidth determining means for determining a bandwidth from preselected values of the waveform and means for determining an amount indicative of pulse pressure from said waveform.

17. The cardiac stimulating apparatus as recited in claim 16, wherein said controller further includes a center frequency determining means for determining a center frequency from predicted values of the waveform.

18. The cardiac stimulating apparatus as recited in claim 17, wherein said controller determines the amount indicative of pulse pressure from the determined bandwidth and center frequency.

19. A cardiac stimulating apparatus functioning in a preset pacing mode having preset pacing rates and timing intervals, and programmed to optimize cardiac performance of a patient's heart, said cardiac stimulating apparatus comprising:
a) a pulse generator;
b) an accelerometer electrically coupled to a controller of the cardiac stimulating apparatus, said accelerometer transmitting a signal associated with fluid and myocardial accelerations of the patient's heart;
c) filtering means coupled to the accelerometer for filtering and conditioning the signal transmitted by the accelerometer to produce a waveform related to a pulse pressure within the patient's heart; and
d) said controller including a timing means for identifying cardiac cycles of the patient's heart and analyzing means for analyzing the amounts indicative of pulse pressure over corresponding cardiac cycles.

20. A cardiac stimulating apparatus functioning in a preset pacing mode having preset pacing rates and timing intervals, and programmed to optimize cardiac performance of a patient's heart, said cardiac stimulating apparatus comprising:

a) a pulse generator;

b) an accelerometer enclosed in a casing of the cardiac stimulating apparatus and electrically coupled to a controller of the cardiac stimulating apparatus, said accelerometer transmitting a signal associated with fluid and myocardial accelerations of the patient's heart;

c) filtering means coupled to the accelerometer for filtering and conditioning the signal transmitted by the accelerometer to produce a waveform related to a pulse pressure within the patient's heart; and d) said controller including a timing means for identifying cardiac cycles of the patient's heart and means for determining an amount indicative of pulse pressure from said waveform, the determined amount indicative of pulse pressure being analyzed and compared by said controller over a preselected number of cardiac cycles for a plurality of preselected timing intervals, said timing intervals being a time between at least one of intrinsic and paced stimulations of preselected chambers of the heart, to thereby determine an optimum timing interval.

21. A cardiac stimulating apparatus functioning in a preset pacing mode having preset pacing rates and timing intervals, and programmed to optimize cardiac performance of a patient's heart, said cardiac stimulating apparatus comprising:

a) a pulse generator;

b) an accelerometer enclosed in a casing of the cardiac stimulating apparatus and electrically coupled to a controller of the cardiac stimulating apparatus, said accelerometer transmitting a signal associated with fluid and myocardial accelerations of the patient's heart;

c) filtering means coupled to the accelerometer for filtering and conditioning the signal transmitted by the accelerometer to produce a waveform related to a pulse pressure within the patient's heart; and d) said controller including a timing means for identifying cardiac cycles of the patient's heart, means for autoregressive analysis of said waveform using algorithms selected from the group consisting of Levinson and Yule-Walker and means for determining an amount indicative of pulse pressure from said waveform.

22. A cardiac stimulating apparatus functioning in a preset pacing mode having preset pacing rates and timing intervals, and programmed to optimize cardiac performance of a patient's heart, said cardiac stimulating apparatus comprising:

a) a pulse generator;

b) an accelerometer enclosed in a casing of the cardiac stimulating apparatus and electrically coupled to a controller of the cardiac stimulating apparatus, said accelerometer transmitting a signal associated with fluid and myocardial accelerations of the patient's heart;

c) filtering means coupled to the accelerometer for filtering and conditioning the signal transmitted by the accelerometer to produce a waveform related to a pulse pressure within the patient's heart; and d) said controller including a timing means for identifying cardiac cycles of the patient's heart and means responsive to the signal transmitted by the accelerometer for identifying a time of physical inactivity, and means for determining an amount indicative of pulse pressure from said waveform.

23. A cardiac stimulating apparatus functioning in a preset pacing mode, said mode selected from the group consisting of A-V pacing, V-V pacing and A-A pacing and having preset pacing rates and timing intervals, and programmed to optimize cardiac performance of a patient's heart, said cardiac stimulating apparatus comprising:

a) a pulse generator;

b) an accelerometer enclosed in a casing of the cardiac stimulating apparatus and electrically coupled to a controller of the cardiac stimulating apparatus, said accelerometer transmitting a signal associated with fluid and myocardial accelerations of the patient's heart;

c) filtering means coupled to the accelerometer for filtering and conditioning the signal transmitted by the accelerometer to produce a waveform related to a pulse pressure within the patient's heart; and d) said controller including a timing means for identifying cardiac cycles of the patient's heart and means for determining an amount indicative of pulse pressure from said waveform.

24. The cardiac stimulating apparatus as recited in claim 23, wherein the A-V pacing mode is selected from the group consisting of $A_R$-$V_R$ pacing, $A_R$-$V_L$ pacing, $A_L$-$V_R$ pacing, $A_R$-$V_{RL}$ pacing, $A_L$-$V_{RL}$ pacing, and $A_L$-$V_L$ pacing.

25. A cardiac stimulating apparatus functioning in a preset pacing mode having preset pacing rates and timing intervals, and programmed to optimize cardiac performance of a patient's heart, said cardiac stimulating apparatus comprising:

a) a pulse generator;

b) an accelerometer enclosed in a casing of the cardiac stimulating apparatus and electrically coupled to a controller of the cardiac stimulating apparatus, said accelerometer transmitting a signal associated with fluid and myocardial accelerations of the patient's heart;

c) filtering means coupled to the accelerometer for filtering and conditioning the signal transmitted by the accelerometer to produce a waveform related to a pulse pressure within the patient's heart; and d) said controller including a timing means for identifying cardiac cycles of the patient's heart, bandwidth determining means for determining a bandwidth from predicted values of the waveform and means for determining an amount indicative of pulse pressure from said waveform.

26. The cardiac stimulating apparatus as recited in claim 25, wherein said controller further includes a center frequency determining means for determining a center frequency from predicted values of the waveform.

27. The cardiac stimulating apparatus as recited in claim 26, wherein said controller determines the amount indicative of pulse pressure from the determined bandwidth and center frequency.

28. A cardiac stimulating apparatus functioning in a preset pacing mode having preset pacing rates and timing intervals, and programmed to optimize cardiac performance of a patient's heart, said cardiac stimulating apparatus comprising:

a) a pulse generator;

b) an accelerometer enclosed in a casing of the cardiac stimulating apparatus and electrically coupled to a controller of the cardiac stimulating apparatus, said accelerometer transmitting a signal associated with fluid and myocardial accelerations of the patient's heart;

c) filtering means coupled to the accelerometer for filtering and conditioning the signal transmitted by the accelerometer to produce a waveform related to a pulse pressure within the patient's heart; and d) said controller including a timing means for identifying cardiac cycles of the patient's heart, means for determining an amount indicative of pulse pressure from said waveform and analyzing means for analyzing the amounts indicative of pulse pressure over corresponding cardiac cycles.

* * * * *